United States Patent
Eichenberger et al.

(10) Patent No.: US 6,600,042 B1
(45) Date of Patent: Jul. 29, 2003

(54) PROCESS FOR THE PREPARATION OF PYRIMIDO[5,4-G]PTERIDINE DERIVATIVES

(75) Inventors: Thomas Eichenberger, Basel (CH); Max Hügin, Rünenberg (CH); Karl-Heinz Müller, Weil am Rhein (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/687,899

(22) Filed: Oct. 13, 2000

(30) Foreign Application Priority Data

Oct. 21, 1999 (CH) ............................................. 1924/99

(51) Int. Cl.[7] ........................................... C07D 487/14

(52) U.S. Cl. ...................................................... 544/251

(58) Field of Search ......................................... 544/251

(56) References Cited

U.S. PATENT DOCUMENTS

| | | | |
|---|---|---|---|
| 2,581,889 A | 1/1952 | Timmis | 260/251.5 |
| 5,525,152 A | 6/1996 | Roschger et al. | 106/498 |
| 6,120,956 A | 9/2000 | Eichenberger et al. | 430/106 |
| 6,126,735 A | 10/2000 | Eichenberger et al. | 106/498 |

FOREIGN PATENT DOCUMENTS

WO 00/31079 6/2000

OTHER PUBLICATIONS

E.C. Taylor et al. "Pyrimidopteridines by Oxidative Self–condensation of Aminopyrimidines" JACS vo. 77, (1955) pp. 2243–2248.

E. Falco et al., "Some Dipyrimidopyrazines", Ciba Foundation Symposium on Chemistry and Biology of Pteridines, (1954), pp. 183–192.

*Primary Examiner*—Deepak Rao
(74) *Attorney, Agent, or Firm*—David R. Crichton

(57) ABSTRACT

Preparation of pyrimido[5,4-g]pteridine of formula I

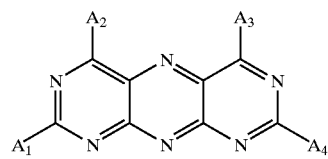

wherein $A_1$, $A_2$, $A_3$ and $A_4$ are each independently of the others $-NR_1R_2$, wherein $R_1$ and $R_2$ are hydrogen, $C_1-C_8$alkyl, $-CO-C_1-C_8$alkyl, $-CO-C_6-C_{14}$aryl, $-COO-C_1-C_8$alkyl, $-COO-C_6-C_{14}$aryl, $-CONH-C_1-C_8$alkyl or $-CONH-C_6-C_{14}$aryl, or $-OH$, $-SH$, hydrogen, $C_1-C_8$alkyl, $C_1-C_8$alkoxy, or $C_6-C_{14}$aryl or $-O-C_6-C_{14}$aryl each unsubstituted or mono- or poly-substituted by halogen, nitro, cyano, $-OR_{10}$, $-SR_{10}$, $-NR_{10}R_{11}$, $-CONR_{10}R_{11}$, $-COOR_{10}$, $-SO_2R_{10}$, $-SO_2NR_{10}R_{11}$, $-SO_3R_{10}$, $-NR_{11}COR_{10}$ or by $-NR_{11}COOR_{10}$, wherein $R_{10}$ and $R_{11}$ are each independently of the other hydrogen, $C_1-C_8$alkyl, $C_5-C_{12}$cycloalkyl or $C_2-C_8$alkenyl, by a) reacting the pyrimidine of formula II

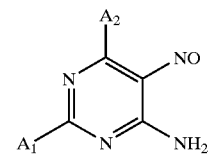

with the pyrimidine of formula III

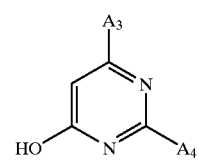

in the presence of an acid and, if desired, of a solvent, the molar ratio of the acid to the compound of formula II being in the range of from 100:1 to 1:1, and b) subsequently treating the resulting reaction mixture with a base, and novel pyrimido[5,4-g]pteridine salts and their use.

9 Claims, No Drawings

PROCESS FOR THE PREPARATION OF PYRIMIDO[5,4-G]PTERIDINE DERIVATIVES

Process for the preparation of pyrimido [5,4-g] pteridine derivatives

The present invention relates to an improved process for the preparation of pyrimido[5,4-g]-pteridine derivatives, to novel pyrimido[5,4-g] pteridine salts and to their use.

JACS 77 (1955) 2243–2248 describes the synthesis of yellow, sparingly soluble pyrimido-pteridines. The synthesis of 2,4,5,7-tetraaminopyrimido[5,4-g]pteridine is unsuitable for industrial use, however, owing inter alia to the process steps of oxidation of the 2,4,5,6-tetra-aminopyrimidine salt with air and separation of the undesired red isomer using a large amount of glacial acetic acid.

From U.S. Pat. No. 2,591,889 there is known the synthesis of pyrimido-pyrazines which may possess fused heterocyclic radicals on the pyrazine ring. For the preparation of those pyrimido-pyrazines, a 5-nitroso-6-aminopyrimidine is condensed with a keto compound. It is said to be advantageous to carry out the preparation in the presence of an acid or alkaline catalyst. Although the process of U.S. Pat. No. 2,591,889 permits the desired positioning of the substituents on the pyrazine ring that forms during the reaction, the poor yields of the process and additional process steps for separating off undesired secondary products are disadvantageous.

The use of pyrimidopteridines for colouring high molecular weight organic material is already known from EP-A-934 363.

Accordingly, the object of the present invention was to make available an improved process for the preparation of pyrimido[5,4-g]pteridines which does not have those disadvantages. In particular, reproducible and high yields are to be obtained. Furthermore, preferably no isomeric mixtures are to be formed in the synthesis of 2,4,5,7-tetraaminopyrimido[5,4-g]pteridine. Moreover, compounds are to be provided which, as colouring agents, have good performance properties.

Accordingly, there has been developed an improved process for the preparation of pyrimido[5,4-g]pteridines of formula I

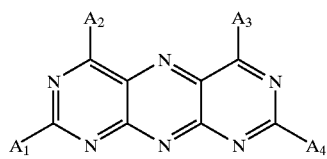

wherein $A_1$, $A_2$, $A_3$ and $A_4$ are each independently of the others

—$NR_1R_2$, wherein $R_1$ and $R_2$ are each independently of the other hydrogen, $C_1$–$C_8$alkyl, —CO—$C_1$–$C_8$alkyl, —CO—$C_6$–$C_{14}$aryl, —COO—$C_1$–$C_8$alkyl, —COO—$C_6$–$C_{14}$aryl, —CONH—$C_1$–$C_8$alkyl or —CONH—$C_6$–$C_{14}$aryl, or —OH, —SH, hydrogen, $C_1$–$C_8$alkyl, $C_1$–$C_8$alkoxy, or $C_6$–$C_{14}$aryl or —O—$C_6$–$C_{14}$aryl each unsubstituted or mono- or poly-substituted by halogen, nitro, cyano, —$OR_{10}$, —$SR_{10}$, —$NR_{10}R_{11}$, —$CONR_{10}R_{11}$, —$COOR_{10}$, —$SO_2R_{10}$, —$SO_2NR_{10}R_{11}$, —$SO_3R_{10}$, —$NR_{11}COR_{10}$ or by —$NR_{11}COOR_{10}$, wherein $R_{10}$ and $R_{11}$ are each independently of the other hydrogen, $C_1$–$C_8$alkyl, $C_5$–$C_{12}$cycloalkyl or $C_2$–$C_8$alkenyl, by a) reacting the pyrimidine of formula II

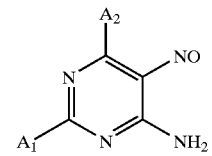

with the pyrimidine of formula III

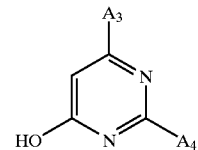

in the presence of an acid and, if desired, of a solvent, the molar ratio of the acid to the compound of formula II being in the range of from 100:1 to 1:1, and b) subsequently treating the resulting reaction mixture with a base.

Salts of the compounds I, processes for their preparation, and the use of the compounds prepared according to the invention have also been found.

$C_1$–$C_8$Alkyl (correspondingly also in —CO—$C_1$–$C_8$alkyl, —COO—$C_1$–$C_8$alkyl, —CONH—$C_1$–$C_8$alkyl) may be, for example, methyl, ethyl, n-propyl, isopropyl, n-butyl, sec-butyl, isobutyl, tert-butyl, n-pentyl, 2-pentyl, 3-pentyl, 2,2-dimethylpropyl, n-hexyl, n-heptyl, n-octyl, 1,1,3,3-tetramethylbutyl or 2-ethylhexyl, preferably $C_1$–$C_4$alkyl, such as methyl, ethyl, n-propyl, isopropyl, n-butyl, sec-butyl, isobutyl or tert-butyl.

$C_6$–$C_{14}$Aryl (correspondingly also in —CO—$C_6$–$C_{14}$aryl, —COO—$C_6$–$C_{14}$aryl and —CONH—$C_6$–$C_{14}$aryl) may be, for example, phenyl, 1-naphthyl, 2-naphthyl, 4-biphenyl, phenanthryl, 2- or 9-fluorenyl or anthracenyl, preferably phenyl, or 1- or 2-naphthyl.

$C_1$–$C_8$Alkoxy may be, for example, methoxy, ethoxy, n-propoxy, isopropoxy, n-butoxy, sec-butoxy, isobutoxy, tert-butoxy, n-pentoxy, 2-pentoxy, 3-pentoxy, 2,2-dimethylpropoxy, n-hexyloxy, n-heptyloxy, n-octyloxy, 1,1,3,3-tetramethylbutoxy or 2-ethylhexyloxy, preferably $C_1$–$C_4$alkoxy, such as methoxy, ethoxy, n-propoxy, isopropoxy, n-butoxy, sec-butoxy, isobutoxy or tert-butoxy.

$C_5$–$C_{12}$Cycloalkyl is preferably cyclopentyl, cyclohexyl, cycloheptyl, cyclooctyl, cyclononyl, cyclodecyl, cycloundecyl or cyclododecyl, especially $C_5$–$C_8$cycloalkyl, such as cyclopentyl, cyclohexyl, cycloheptyl or cyclooctyl.

$C_2$–$C_8$Alkenyl is preferably ethenyl, 1- or 2-propenyl, 1-, 2- or 3-butenyl, 2-methyl-1-propenyl, 2-methyl-2-propenyl, 1-pentenyl, 2-pentenyl, 3-pentenyl, 1-hexenyl, 1-heptenyl, 1-octenyl or 2-ethyl-1-hexenyl, especially $C_2$–$C_4$alkenyl, such as ethenyl, 1- or 2-propenyl, 1-, 2- or 3-butenyl, 2-methyl-1-propenyl or 2-methyl-2-propenyl.

The order in which the compounds of formulae II and III and the acid are added is generally not critical. However, it has proved advantageous first to introduce the compounds of formulae II and III and then to add the acid.

The molar ratio of pyrimidine II to pyrimidine III is generally chosen in the range of from 2:1 to 1:2, preferably from 1.5:1 to 1:1.

The molar amount of base is generally so chosen that the pH value of the reaction mixture obtained in process step a)

is neutral. For example, the molar ratio of the base to the compound of formula II is generally chosen in the range of from 1:1 to 20:1, preferably from 1:1 to 10:1.

If the reaction is carried out in a solvent, the molar ratio of the solvent to the compound II is generally chosen in the range of from 500:1 to 1:2, preferably from 100:1 to 1:1.

The reaction temperature in process step a) is dependent inter alia on the solvent that is used, if desired, and is generally in the range of from 50 to 200° C., preferably from 90 to 140° C., especially in the region of the boiling temperature of the solvent used.

The reaction temperature in process step b) is likewise usually dependent on the solvent that is present, if desired, and is generally in the range of from 70 to 130° C., preferably from 80 to 100° C.

The chosen reaction pressure in process steps a) and b) is preferably atmospheric pressure, but the reaction may alternatively be carried out at higher or lower pressures, for example in the range of from 50 kPa to 5 MPa.

The reaction time of both process steps a) and b) is usually dependent on the chosen reaction temperature and the reactivity of the starting materials. In general, a time in the range of from 1 to 50 hours, preferably from 3 to 24 hours, is chosen.

The base is usually added to the reaction mixture obtained in step a). However, it is also possible to introduce the base first and add the reaction mixture obtained in step a) thereto. The addition of the base may take place continuously or discontinuously in equal or unequal portions.

In a further embodiment of the process according to the invention, the addition of the base may be carried out with pH monitoring using the apparatuses for potentiometric pH determination conventionally employed therefor.

There may be used as solvents organic solvents or water, as well as mixtures of organic solvents and mixtures of organic solvents with water. Suitable organic solvents are, for example, polar aprotic or polar protic solvents.

Polar aprotic solvents are, for example, N,N'-dimethylformamide, N,N'-dimethylacetamide, N-methylpyrrolidone and diethylene glycol dimethyl ether.

Polar protic solvents are, for example, glycols and their ether derivatives, wherein at least one hydroxy group of the glycol is not etherified, such as mono-, di-, tri- or tetra-ethylene glycol, propylene glycol, their methyl, ethyl and butyl ethers, such as ethylene glycol, ethylene glycol monomethyl ether, ethylene glycol monoethyl ether, diethylene glycol monomethyl ether or diethylene glycol monoethyl ether, and alcohols, such as methanol, ethanol, propanol, sec-propanol or butanol.

Preference is given to water and organic polar, protic solvents.

There may be used as acids generally inorganic acids, such as hydrochloric acid, hydrobromic acid, hydriodic acid, iodic acid, phosphoric acid, arylphosphoric acids, such as phenylphosphoric acid, alkylphosphoric acids, such as methylphosphoric acid, ethylphosphoric acid and n-propylphosphoric acid, hypophosphoric acid, polyphosphoric acid, boric acid, arylboric acids, such as phenylboric acid, alkylboric acids, such as methylboric acid, or sulfamic acids, such as sulfamic acid or methyl-, ethyl-, n-propyl-, isopropyl-, n-butyl-, sec-butyl-, isobutyl- or tert-butyl-sulfamic acids, sulfurous acid and sulfuric acid, or organic acids, such as $C_1$–$C_4$alkane acids, such as methane-, ethane-, n-propane-, isopropane-, n-butane-, sec-butane-, isobutane- and tert-butane-acids, preferably acetic acid and propionic acid, especially glacial acetic acid, or di-$C_1$–$C_4$alkane carboxylic acids, such as oxalic acid, as well as halogenated alkane acids, such as chloroacetic acid or trifluoroacetic acid, or sulfonic acids, such as arylsulfonic acids, such as phenylsulfonic acid or methyl-, ethyl-, n-propyl-, isopropyl-, n-butyl-, sec-butyl-, isobutyl- or tert-butyl-substituted p-phenylsulfonic acid, such as, especially, p-toluene- or benzene-1,3-disulfonic acid, also 1-naphthyl, 2-naphthyl, 1-anthraquinoyl, 2-anthraquinoyl, or alkylsulfonic acids, such as methyl-, ethyl-, n-propyl-, isopropyl-, n-butyl-, sec-butyl-, isobutyl- and tert-butyl-sulfonic acids, taurine, and mixtures of those acids.

It has proved advantageous to use those acids which have a $pK_a$ value less than or equal to that of the solvent that is used, if desired.

Preferred acids are sulfamic acid, sulfonic acids or phosphoric acid as well as $C_1$–$C_4$alkylcarboxylic acids.

Special preference is given to sulfamic acid, methanesulfonic acid, benzenesulfonic acid or p-toluenesulfonic acid as well as $C_1$–$C_4$alkylcarboxylic acids, especially formic acid, acetic acid or propionic acid.

Very special preference is given to p-toluenesulfonic acid or benzenesulfonic acid as well as $C_1$–$C_4$alkylcarboxylic acids, especially acetic acid (especially in the form of glacial acetic acid) or propionic acid.

Suitable bases are generally organic or inorganic bases. Organic bases are, for example, organic amines, such as triethylamine, dialkylamine, tetrabutylammonium hydroxide, piperidine, pyrrolidine, pyridine, morpholine, N,N'-dimethylaniline, or aliphatic alcoholates, such as sodium methoxide, ethoxide, propoxide or butoxide or potassium tert-butoxide, or aromatic alcoholates, such as phenolate, or carboxylic acid salts, for example sodium or potassium acetate. Inorganic bases are, for example, alkali metal or alkaline earth metal oxides, hydroxides, hydrides or carbonates, such as sodium, potassium or caesium hydroxide, sodium or potassium hydride, calcium oxide, magnesium oxide, sodium carbonate, potassium carbonate, sodium hydrogen carbonate or ammonia.

Bases are preferably alkali metal or alkaline earth metal hydroxides, such as sodium hydroxide or potassium hydroxide, or magnesium hydroxide, or alkali metal carbonates, such as sodium carbonate, potassium carbonate, or alkali metal hydrogen carbonates, such as sodium hydrogen carbonate.

Special preference is given to the use of sodium hydroxide or potassium hydroxide as bases.

The reaction may be carried out under a protecting gas atmosphere. Noble gases, preferably helium and argon, as well as nitrogen may be used as protecting gases.

The compounds of formula I may generally be isolated by the customary methods, such as by filtration.

In general, it is possible to carry out the filtration in generally customary apparatuses. There are suitable, for example, suction filters, pressure suction filters, centrifuges, filters, fluted filters and presses.

If desired, the filtration residue may subsequently be washed.

Solvents suitable for washing are, for example, water and/or organic solvents, especially alcohols, such as methanol.

The temperature of the solvent used for washing is generally in the range of from 10 to 80° C. and preferably in the range of from 40 to 80° C.

It has proved advantageous to use for washing an amount of solvent that is sufficient to adjust the pH of the washing filtrate to a value in a pH range of from 4 to 7, preferably from 5 to 7.

If desired, the filtration residue, comprising the compound of formula I, may be dried. Generally known drying apparatuses, such as drying cabinets, paddle dryers, spray dryers or freeze dryers, are generally used for that purpose.

In a preferred form of the process according to the invention $A_1$, $A_2$, $A_3$ and $A_4$ in the compound of formula I are each independently of the others hydrogen, hydroxy, methoxy, ethoxy, methyl, ethyl, phenyl, p-aminophenyl, p-amino-aminophenyl, dimethylaminophenyl and p-diethylaminophenyl, $NH_2$, $NHR_{12}$ or $R_{13}$, wherein $R_{12}$ and $R_{13}$ are hydrogen, methyl, ethyl, phenyl, p-aminophenyl, p-dimethylaminophenyl, p-diethylaminophenyl, p-methoxyphenyl or p-ethoxyphenyl.

Special preference is given to the process according to the invention wherein at least two of the radicals $A_1$, $A_2$, or $A_1$, $A_3$, or $A_1$, $A_4$, or $A_2$, $A_3$, or $A_2$, $A_4$, or $A_3$, $A_4$ in the compound of formula I are each independently of the other(s) $NH_2$, $NHR_{12}$ or $R_{13}$.

Very special preference is given to the process according to the invention wherein $A_1$, $A_2$, $A_3$ and $A_4$ are $NH_2$.

The pyrimidines II and III are known and available commercially, or can be prepared, for example, analogously to the processes as described in Volume 52 "The Pyrimidines" of "The Chemistry of Heterocyclic Compounds", A Series of Monographs, John Wiley & Sons 1994.

In a preferred form, treatment with a base b) is carried out not with the reaction mixture obtained in step a) but with the reaction product separated from the reaction mixture. The separation may be carried out by processes known per se, such as decantation or filtration, preferably by filtration.

In general, filtration may be carried out by generally customary methods using customary apparatuses. There are suitable, for example, suction filters, pressure suction filters, centrifuges, filters, fluted filters or presses.

If desired, the filtration residue may subsequently be washed. Organic solvents and/or water are generally used for washing. Water and alcohols, and especially water, are preferred.

It is usually recommended to use for washing an amount of solvent that is sufficient to adjust the pH value of the washing water to greater than pH 4.

In a preferred form of the process according to the invention, the reaction product is separated from the reaction mixture at a temperature of from 20 to 100° C., preferably from 60 to 100° C., preferably by filtration.

If desired, the separated reaction product may be dried after it has been washed. Suitable drying apparatuses are those generally known, such as drying cabinets or paddle dryers.

The drying temperature is generally in the range of from 40 to 120° C.

It has proved advantageous to use a mixture of solvent and base in step b). It is possible to add that mixture to the separated reaction product or, conversely, to add the separated reaction product to the mixture. It has proved especially advantageous to add the reaction product to the mixture of solvent and base.

The molar ratio of the solvent to the compound I is generally chosen in the range of from 500:1 to 1:2, preferably from 100:1 to 1:1.

In general, the separated reaction product, the solvent and the base may be mixed or kneaded together by generally customary methods.

For example, customary mixing apparatuses, such as stirrers, kneaders or mixers, may be employed.

It has proved especially advantageous to use intensive mixers, for example from the ULTRA-TURRAX® range (JANKE-&KUNKEL GmbH & Co, Staufen, Germany).

A further form of the process according to the invention relates to the preparation of pyrimido[5,4-g]pteridine of formula I by reaction of an organic salt with a base in the presence of a solvent, by reacting the pyrimido[5,4-g]pteridine salt of formula IV

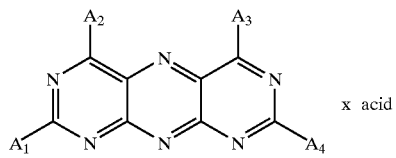

IV x acid with a base in the presence of a solvent, with the proviso that when $A_1$, $A_2$, $A_3$ and $A_4$ are $NH_2$, the acid is not phosphoric acid, sulfamic acid or $R_{14}NSO_3H$, wherein $R_{14}$ is hydrogen or $C_1$–$C_4$alkyl.

The process parameters and amounts for the reaction with solvent and base correspond to those mentioned hereinbefore.

There may be used as acids generally inorganic acids, such as hydrochloric acid, hydrobromic acid, hydriodic acid, iodic acid, phosphoric acid, arylphosphoric acids, such as phenylphosphoric acid, alkylphosphoric acids, such as methylphosphoric acid, ethylphosphoric acid, n-propylphosphoric acid, hypophosphoric acid, polyphosphoric acid, boric acid, arylboric acids, such as phenylboric acid, alkylboric acids, such as methylboric acid, or sulfamic acids, such as sulfamic acid or methyl-, ethyl-, n-propyl-, isopropyl-, n-butyl-, sec-butyl-, isobutyl- or tert-butyl-sulfamic acids, sulfurous acid and sulfuric acid, or organic acids, such as $C_1$–$C_4$alkane acids, such as methane-, ethane-, n-propane-, isopropane-, n-butane-, sec-butane-, isobutane- and tert-butane acids, or dialkane carboxylic acids, such as oxalic acid, as well as halogenated alkane acids, such as chloroacetic acid or trifluoroacetic acid, or sulfonic acids, such as arylsulfonic acids, such as phenylsulfonic acid or methyl-, ethyl-, n-propyl-, isopropyl-, n-butyl-, sec-butyl-, isobutyl- or tert-butyl-substituted p-phenylsulfonic acid, such as, especially, p-toluene- or benzene-1,3-disulfonic acid, also 1-naphthyl, 2-naphthyl, 1-anthraquinoyl, 2-anthraquinoyl, or alkylsulfonic acids, such as methyl-, ethyl-, n-propyl-, isopropyl-, n-butyl-, sec-butyl-, isobutyl- and tert-butyl-sulfonic acids, and taurine.

Preferred acids are sulfamic acid, sulfonic acids or phosphoric acid as well as $C_1$–$C_4$alkylcarboxylic acids.

Special preference is given to sulfamic acid, methanesulfonic acid, benzenesulfonic acid or p-toluenesulfonic acid as well as $C_1$–$C_4$alkylcarboxylic acids, especially formic acid, acetic acid and propionic acid.

Very special preference is given to p-toluenesulfonic acid or benzenesulfonic acid as well as $C_1$–$C_4$alkylcarboxylic acids, especially acetic acid (especially in the form of glacial acetic acid) or propionic acid.

A preferred form of the process relates to the preparation of pyrimido[5,4-g]pteridine salts of formula IV by reacting the pyrimidine of formula II with the pyrimidine of formula III in the presence of an acid and, if desired, of a solvent, the molar ratio of the acid to the compound of formula II being in the range of from 100:1 to 1:1.

The process parameters and details regarding starting materials and amounts employed correspond to process step a) above for the preparation of the compound of formula I.

The pyrimido[5,4-g]pteridine salt of formula IV may be worked up by the customary methods, for example by filtration, if desired with subsequent washing and drying of the filtration residue.

The salts of the pyrimido[5,4-g]pteridines of formula IV can also be prepared by reacting the pyrimido[5,4-g] pteridines of formula I with an acid.

The present invention relates also to pyrimido[5,4-g] pteridine salts of formula IV which are obtainable by the processes according to the invention.

The pyrimido[5,4-g]pteridine salts of formula IV may also be reacted directly to form pyrimido[5,4-g]pteridines of formula I without being isolated.

The invention relates also to a process for the preparation of pyrimido[5,4-g]pteridines of formula I by
 a) reacting the pyrimidine of formula II with the pyrimidine of formula III in the presence of a solvent and of an acid to form the compound of formula V

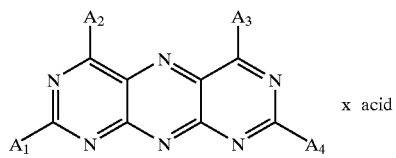

and
 b) subsequently treating the compound of formula V with a base.

The process parameters and details regarding starting materials and amounts employed correspond to the above process steps for the preparation of the compound of formula I.

The molar ratio of the acid to II or III is generally chosen in the range of from 1:1 to 100:1, preferably from 1:1 to 5:1, and especially in the range of from 1:1 to 2:1.

The invention relates also to pyrimido[5,4-g]pteridine salts of formula IV

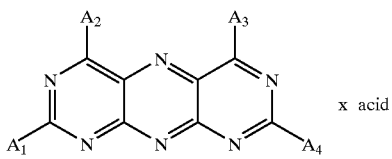

with the proviso that when $A_1$, $A_2$, $A_3$ and $A_4$ are $NH_2$, the acid is not phosphoric acid, sulfamic acid or $R_{14}NSO_3H$, wherein $R_{14}$ is hydrogen or $C_1$–$C_4$alkyl.

Preference is given to pyrimido[5,4-g]pteridine salts of formula IV wherein the acid is sulfamic acid, sulfamic acid, a sulfonic acid, a $C_1$–$C_4$alkylcarboxylic acid or phosphoric acid, especially sulfamic acid or a sulfonic acid, such as benzenesulfonic acid, methanesulfonic acid or p-toluenesulfonic acid, or a $C_1$–$C_4$alkylcarboxylic acid, such as acetic acid or propionic acid, and more especially a sulfonic acid, such as p-toluenesulfonic acid or benzenesulfonic acid, as well as a $C_1$–$C_4$alkylcarboxylic acid, especially acetic acid, with the proviso that when $A_1$, $A_2$, $A_3$ and $A_4$ are $NH_2$, the acid is not phosphoric acid or sulfamic acid.

Special preference is given to the pyrimido[5,4-g] pteridine salt IV wherein $A_1$, $A_2$, $A_3$ and $A_4$ are $NH_2$ and the acid is sulfonic acid or a $C_1$–$C_4$alkylcarboxylic acid.

Very special preference is given to the pyrimido[5,4-g] pteridine salt of formula IV wherein $A_1$, $A_2$, $A_3$ and $A_4$ are $NH_2$ and the acid is a sulfonic acid, preferably p-toluenesulfonic acid or benzenesulfonic acid, or a $C_1$–$C_4$alkylcarboxylic acid, especially acetic acid.

The pyrimido[5,4-g]pteridine I according to the invention is preferably used as a colouring agent, especially as a pigment, according to methods which are in each case generally known per se.

The pyrimido[5,4-g]pteridine I is suitable especially for the colouring of high molecular weight organic materials. The pyrimido[5,4-g]pteridine I is also suitable for the production of toners and printing inks for various applications, such as intaglio/flexographic printing, sheet offset printing and tin printing, as well as for the production of colour filters.

In the case of intaglio/flexographic printing, a printing ink is customarily prepared from a printing ink concentrate by dilution with a solvent (water and/or an organic solvent), which printing ink can then be used according to methods known per se.

The printing ink concentrate is generally prepared by mixing the pyrimido[5,4-g]pteridine I with a clear lacquer, it being possible for the clear lacquer to be prepared, for example, from nitrocellulose, ethanol and other customary additives.

In a preferred embodiment, the printing ink concentrate comprises the pyrimido[5,4-g]-pteridine I in an amount in the range of from 15 to 40% by weight, based on the concentrate, and the amount of the pyrimido[5,4-g]pteridine I in the printing ink is generally chosen in the range of from 10 to 20% by weight, based on the printing ink, according to the desired application.

When the pyrimido[5,4-g]pteridine I is used in sheet offset printing and tin printing, the pyrimido[5,4-g]pteridine I is generally used in an amount in the range of from 15 to 30% by weight, preferably from 20 to 25% by weight, based on the pigment-containing printing ink.

The high molecular weight organic material to be coloured according to the invention ($M_w$=from $10^3$ to $10^9$ g/mol) may be of natural or synthetic origin. It may be, for example, natural resin or drying oils, rubber or casein, or modified natural materials, such as chlorinated rubber, oil-modified alkyd resins, viscose, cellulose ethers or esters, such as cellulose acetate, cellulose propionate, cellulose acetobutyrate or nitrocellulose, but especially fully synthetic organic polymers (both thermosetting plastics and thermoplastics), as are obtained by polymerisation, polycondensation or polyaddition. From the class of the polymerisation resins there may be mentioned especially polyolefins, such as polyethylene, polypropylene or polyisobutylene, also substituted polyolefins, such as polymers of vinyl chloride, vinyl acetate, styrene, acrylonitrile, acrylic acid and/or methacrylic acid esters or butadiene, as well as copolymers of the mentioned monomers, especially ABS (acrylonitrile/butadiene/styrene) or EVA (ethylene/vinyl acetate).

From the group of the polyaddition resins and polycondensation resins there may be mentioned the condensation products of formaldehyde with phenols, the so-called phenolic resins, and the condensation products of formaldehyde with urea, thiourea and melamine, the so-called aminoplastic resins, polyesters used as surface coating resins, both saturated, such as alkyd resins, and unsaturated, such as maleic resins, also linear polyesters and polyamides or silicones.

The mentioned high molecular weight compounds may be present individually or in mixtures, in the form of plastic compositions or melts, which may optionally be spun to form fibres.

They may also be present in the form of their monomers or in the polymerised state in dissolved form as film-forming agents or binders for surface coatings or printing inks, such as boiled linseed oil, nitrocellulose, alkyd resins, melamine resins, urea-formaldehyde resins or acrylic resins.

Pigmenting of the high molecular weight organic substances with the pyrimido[5,4-g]pteridines I according to the invention is carried out, for example, by adding such a pigment, where appropriate in the form of a masterbatch, to those substrates using, for example, rolling mills, mixing or grinding apparatuses. The pigmented material is then generally brought into the desired final form by processes known per se, such as calendering, compression moulding, extrusion, spread-coating, casting or by injection moulding. It is often desirable, in order to produce mouldings that are not rigid or to reduce their brittleness, to incorporate so-called plasticisers into the high molecular weight compounds before they are shaped. There may be used as plasticisers, for example, esters of phosphoric acid, phthalic acid or sebacic acid. The plasticisers may be incorporated in the process according to the invention before or after the incorporation of the pigment colouring into the polymers. It is also possible, in order to achieve different shades of colour, to add to the high molecular weight organic substances, in addition to the pyrimido[5,4-g]pteridines of formula I, also fillers or other constituents imparting colour, such as white, coloured or black pigments as well as effect pigments, in each case in the desired amount.

For the pigmenting of surface coatings and printing inks, the high molecular weight organic materials and the pyrimido[5,4-g]pteridines of formula I, where appropriate together with additives such as fillers, other pigments, siccatives or plasticisers, are generally finely dispersed or dissolved in an organic and/or aqueous solvent or solvent mixture. The procedure may be such that the individual components are dispersed or dissolved separately or several are dispersed or dissolved together, and only then are all the components combined.

Accordingly, a further embodiment relates also to mass coloured high molecular weight organic material comprising a pyrimido[5,4-g]pteridine of formula I, the said material comprising (a) from 0.05 to 20% by weight, based on the sum of (a) and (b), of pyrimido[5,4-g]pteridine of formula I, and (b) from 99.95 to 80% by weight, based on the sum of (a) and (b), of a high molecular weight organic material, as well as (c) additives, if desired.

Accordingly, a further embodiment relates also to the use of the pyrimido[5,4-g]pteridines of formula I in the mass colouring of high molecular weight organic material in a manner known per se, for example by mixing together the pyrimido[5,4-g]pteridines I and the high molecular weight organic material.

The resulting colourings, for example in plastics, fibres, surface coatings or prints, are distinguished by a green-tinged yellow colour, a very high colour strength, high saturation, good dispersibility, and good fastness to overspraying, migration, heat, light and weathering.

The processes of the present invention are also distinguished by good yields. With the processes according to the invention it is possible in a targeted manner to achieve a desired positioning of substituents on the pyrazine ring that forms during the reaction. The formation of isomers can be prevented.

EXAMPLES

Example 1

A suspension of 6.20 g of commercial 2,4,6-triamino-5-nitrosopyrimidine (Chemie Uetikon, Lahr, Germany), 5.15 g of commercial 2,4-diamino-6-hydroxypyrimidine (Fluka, Buchs, Switzerland) and 11.52 g of commercial toluene-4-sulfonic acid monohydrate in 110 ml of glacial acetic acid (100%) is stirred for 20 hours at 113° C. The reaction mixture is filtered off over a laminated paper filter while still hot, and the residue is washed with hot water (approx. 60° C.) until the pH of the washing water has reached a value of at least 4. The washed residue, moist with water, is dried in vacuo at 110° C. to yield a greenish-yellow powder of the pyrimido[5,4-g]pteridine salt of formula VI

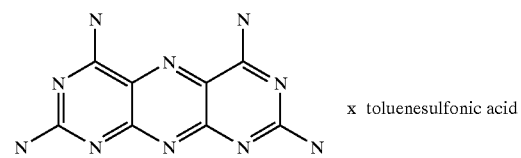

VI x toluenesulfonic acid

Elemental Composition

|  | C | H | N | S |
|---|---|---|---|---|
| (calc. for $C_{15}H_{16}N_{10}O_3S \cdot 0.4H_2O$: | C: 42.55%<br>C: 42.53% | H: 4.01%<br>H: 4.00% | N: 33.22%<br>N: 33.06% | S: 7.41%<br>S: 7.57%) |

Example 2

A suspension of 6.20 g of commercial 2,4,6-triamino-5-nitrosopyrimidine, 5.15 g of commercial 2,4-diamino-6-hydroxypyrimidine and 11.52 g of commercial toluene-4-sulfonic acid monohydrate in 110 ml of glacial acetic acid (100%) is stirred for 20 hours at 113° C. The reaction mixture is filtered off over a laminated paper filter while still hot, and the residue is washed with hot water (approx. 60° C.) until the pH of the washing water has reached a value of at least 4. The washed residue, moist with water, is dispersed over a period of one minute in a mixture of 250 ml of water and 20 ml of 30% by weight aqueous sodium hydroxide solution by means of an ULTRA-TURRAX® stirring rod. The reaction mixture is then heated to a temperature in the range of from 90 to 95° C. and stirred at that temperature for 20 hours. The reaction mixture is then filtered over a glass fibre/laminated paper filter while still hot, and the filtration residue is washed with hot water until the washing water is neutral (pH paper) and is dried in vacuo at 110° C. There are obtained 8.3 g (85% of the theoretical yield) of a yellow powder having the following elemental composition:

|  | C | H | N |
|---|---|---|---|
| (calc. for $C_8H_8N_{10} \cdot 0.3H_2O$: | C: 38.56%<br>C: 38.49% | H: 3.54%<br>H: 3.47% | N: 55.34%<br>N: 56.11%) |

Example 3

A mixture of 6.20 g of commercial 2,4,6-triamino-5-nitrosopyrimidine, 5.15 g of 2,4-diamino-6- hydroxypyrimidine and 3.92 g of sulfamic acid in 230 ml of water is finely stirred for one minute by means of an ULTRA-TURRAX® stirring rod and heated to a temperature in the range of from 82 to 86° C. Stirring is carried out at that temperature for 17 hours, and then 40 ml of 30% by weight aqueous sodium hydroxide solution are added and the mixture is stirred for a further 24 hours. The resulting suspension is filtered over a laminated paper filter while still hot, and the residue is washed with hot water until the washing water is neutral and is then dried in vacuo at 110° C. There are obtained 5.56 g (57% of the theoretical yield) of a yellow powder having the following elemental composition:

| | C: 37.94% | H: 3.56% | N: 54.98% |
|---|---|---|---|
| (calc. for $C_8H_8N_{10} \cdot 0.5H_2O$: | C: 37.94% | H: 3.58% | N: 55.31%) |

Example 4

A mixture of 6.20 g of commercial 2,4,6-triamino-5-nitrosopyrimidine, 5.15 g of 2,4-diamino-6-hydroxypyrimidine and 3.92 g of sulfamic acid in 230 ml of water is finely stirred for one minute by means of an ULTRA-TURRAX® stirring rod and heated to a temperature in the range of from 82 to 86° C. The mixture is stirred at that temperature for 17 hours and then filtered over a laminated paper filter while still hot. The residue is washed with hot water until the pH of the washing water is above 4. After drying in vacuo at 110 ° C., there are obtained 10.28 g (75% of the theoretical yield) of a light-yellow powder of the pyrimido-[5,4-g]pteridine salt of formula IV, the acid being sulfamic acid.

Example 5

The light-yellow powder, 10.28 g, prepared according to Example 4 is finely stirred for 5 minutes in 220 ml of 1N aqueous sodium hydroxide solution by means of an ULTRA-TURRAX® stirring rod and heated to a temperature in the range of from 83 to 87° C. Stirring is carried out at that temperature for 21 hours. The mixture is then filtered over a glass fibre/laminated paper filter while still hot and washed with hot water until the pH of the washing water is neutral. After drying in vacuo at 110° C., there are obtained 4.74 g (64% of the theoretical yield, based on the sulfamic acid salt) of a yellow powder having the following elemental composition:

| | C: 37.89% | H: 3.57% | N: 53.89% |
|---|---|---|---|
| (calc. for $C_8H_8N_{10} \cdot 0.6H_2O$: | C: 37.68% | H: 3.64% | N: 54.92%) |

Example 6

A suspension of 6.20 g of commercial 2,4,6-triamino-5-nitrosopyrimidine, 5.15 g of commercial 2,4-diamino-6-hydroxypyrimidine and 7.69 g of commercial toluene-4-sulfonic acid monohydrate in 150 ml of ethylene glycol is stirred for 20 hours at from 110 to 115° C. The reaction mixture is filtered off over a laminated paper filter while still hot, and the residue is washed with 300 ml of hot water (approx. 60° C.). The washed residue, moist with water, is dispersed over a period of 5 minutes in 240 ml of 1N aqueous sodium hydroxide solution by means of an ULTRA-TURRAX® stirring rod. The reaction mixture is then heated to a temperature in the range of from 90 to 95° C. and stirred at that temperature for 23 hours. The reaction mixture is then filtered over a glass fibre/laminated paper filter while still hot, washed with hot water until the washing water is neutral (pH paper) and dried in vacuo at 110° C. There are obtained 5.60 g (57% of the theoretical yield) of a yellow powder having the following elemental composition:

| | C: 37.47% | H: 3.27% | N: 53.55% |
|---|---|---|---|
| (calc. for $C_8H_8N_{10} \cdot 0.7H_2O$: | C: 37.41% | H: 3.69% | N: 54.54%) |

Example 7

A mixture of 37.0 g of commercial 2,4,6-triamino-5-nitrosopyrimidine and 30.5 g of commercial 2,4-diamino-6-hydroxypyrimidine is heated to from 127 to 130° C. (pressure vessel) in the course of 2 hours in 520 ml of glacial acetic acid (100%), with stirring, and stirred at that temperature for 16 hours. The reaction mixture is cooled to 80° C., filtered over a glass fibre/laminated paper filter and washed first with 300 ml of warm (60° C.) glacial acetic acid and then with 500 ml of water. The filter cake, moist with water, is stirred into 1200 ml of water, adjusted to a pH of 8 by means of pH meter by the addition of 50% by weight aqueous sodium hydroxide solution, and heated to 95° C. in the course of one hour. The pH of the reaction mixture is then adjusted to 10.8, and stirring is carried out for 18 hours at that pH and 95° C. The reaction mixture is then filtered over a glass fibre/laminated paper filter while hot. The filter cake, moist with water, is again stirred into 1000 ml of hot (90° C.) water, again filtered over a glass fibre/laminated paper filter, and finally washed with sufficient hot water until the pH of the washing water is neutral. After drying in vacuo at 60° C. there are obtained 42.6 g (79% of the theoretical yield) of a yellow powder of formula I, wherein $A_1=A_2=A_3=A_4=NH_2$, having the following elemental composition:

| | C: 37.69% | H: 3.44% | N: 54.82% |
|---|---|---|---|
| (calculated for $C_8H_8N_{10} \cdot 0.6H_2O$): | C: 37.68% | H: 3.64% | N: 54.92% |

Example 8

A suspension of 6.27 g of commercial 2,4,6-triamino-5-nitrosopyrimidine, 5.19 g of commercial 2-amino-4,6-dihydroxypyrimidine and 7.76 g of p-toluenesulfonic acid monohydrate (Fluka, Buchs, Switzerland) in 150 ml of glacial acetic acid (100%) is heated to a temperature in the range of from 113 to 116° C. and stirred at that temperature for 20 hours. The mixture is filtered over a hard filter while hot and washed first with 50 ml of glacial acetic acid and then with 100 ml of water. The filter cake is then stirred into 200 ml of water over a period of 5 minutes by means of an ULTRA-TURRAX® stirring rod, and the suspension, which has a pH of approximately 4, is brought to a pH of 11 by the addition of 30% aqueous sodium hydroxide solution and stirred for 30 minutes, the vigorous formation of foam being suppressed by the addition of 1 ml of n-butanol. The pH is then adjusted to from 8 to 9 by the addition of dilute phosphoric acid, and the suspension is heated to 90° C. and stirred at that temperature for 3 hours; during that time, the pH is always kept at approximately 8 by the addition of a small amount of sodium hydroxide solution, if necessary. The mixture is then filtered over a hard filter and the residue is washed with 300 ml of hot (80° C.) water. After drying in vacuo at 100° C. there are obtained 2.82 g (29% of the theoretical yield) of a yellowish-brown powder of formula VII

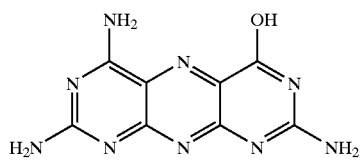

having the following elemental composition:

|  | C: 36.91% | H: 3.93% | N: 46.72% |
|---|---|---|---|
| (calculated for $C_8H_7N_9O \cdot H_2O$): | C: 36.50% | H: 3.45% | N: 47.89% |

What is claimed is:

1. A process for the preparation of pyrimido[5,4-g] pteridine of formula I

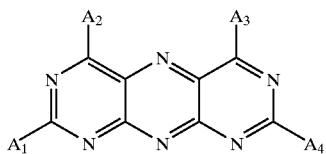

wherein
$A_1$, $A_2$, $A_3$ and $A_4$ are each independently of the others —$NR_1R_2$, wherein $R_1$ and $R_2$ are each independently of the other hydrogen, $C_1$-$C_8$alkyl, phenyl, p-aminophenyl, p-dimethylaminophenyl, p-diethylaminophenyl, p-methoxyphenyl, p-ethoxyphenyl, —CO—$C_1$-$C_8$alkyl, —CO—$C_6$-$C_{14}$aryl, —COO—$C_1$-$C_8$alkyl, —COO—$C_6$-$C_{14}$aryl, —CONH—$C_1$-$C_8$alkyl or —CONH—$C_6$-$C_{14}$aryl, which process comprises a) reacting the pyrimidine of formula II

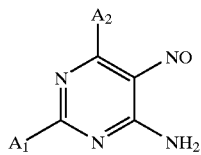

with the pyrimidine of formula III

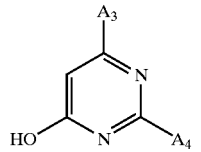

in the presence of an acid and optionally in the presence of a solvent, the molar ratio of the acid to the compound of formula II being in the range of from 100:1 to 1:1, and b) subsequently treating the resulting reaction mixture with a base.

2. A process for the preparation of pyrimido[5,4-g] pteridine of formula I according to claim 1, wherein, instead of step b), the reaction product is separated from the reaction mixture according to step a) and the separated reaction product is then treated with a base in the presence of a solvent.

3. A process according to claim 1, wherein in formula I $A_1$, $A_2$, $A_3$ and $A_4$ are each independently of the others $NH_2$, $NHR_{12}$ or $NR_{12}R_{13}$, wherein $R_{12}$ and $R_{13}$ are hydrogen, methyl, ethyl, phenyl, p-aminophenyl, p-dimethylaminophenyl, p-diethylaminophenyl, p-methoxyphenyl or p-ethoxyphenyl.

4. A process according to claim 1, wherein in formula I $A_1$, $A_2$, $A_3$ and $A_4$ are $NH_2$.

5. A process for the preparation of pyrimido[5,4-g] pteridine of formula I according to claim 1, which comprises a) reacting the pyrimidine of formula II according to claim 1 with the pyrimidine of formula III according to claim 1 in the presence of an acid and optionally in the presence of a solvent to form the compound of formula V

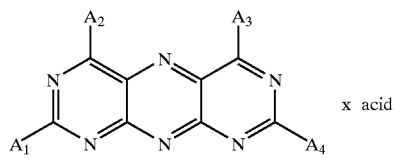

wherein $A_1$, $A_2$, $A_3$ and $A_4$ are as defined in claim 1, and b) subsequently treating the compound of formula V with a base.

6. A process according to claim 2, wherein in formula I $A_1$, $A_2$, $A_3$ and $A_4$ are each independently of the others $NH_2$, $NHR_{12}$ or $NR_{12}R_{13}$, wherein $R_{12}$ and $R_{13}$ are hydrogen, methyl, ethyl, phenyl, p-aminophenyl, p-dimethylaminophenyl, p-diethylaminophenyl, p-methoxyphenyl or p-ethoxyphenyl.

7. A process according to claim 2, wherein in formula I $A_1$, $A_2$, $A_3$ and $A_4$ are $NH_2$.

8. A process according to claim 3, wherein in formula I $A_1$, $A_2$, $A_3$ and $A_4$ are $NH_2$.

9. A process for the preparation of pyrimido[5,4-g] pteridine of formula I

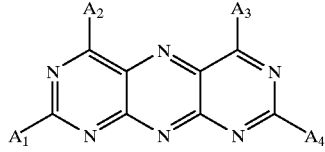

wherein
$A_1$, $A_2$, $A_3$ and $A_4$ are each independently of the others —$NR_1R_2$, wherein $R_1$ and $R_2$ are each independently of the other hydrogen, $C_1$-$C_8$alkyl, phenyl, p-aminophenyl, p-dimethylaminophenyl, p-diethylaminophenyl, p-methoxyphenyl, p-ethoxyphenyl, —CO—$C_1$-$C_8$alkyl, —CO—$C_6$-$C_{14}$aryl, —COO—$C_1$-$C_8$alkyl, —COO—$C_6$-$C_{14}$aryl, —CONH—$C_1$-$C_8$alkyl or —CONH—$C_6$-$C_{14}$aryl, by reaction of an organic salt with solvent and base, which process comprises reacting the pyrimido[5,4-g]-pteridine salt of formula IV

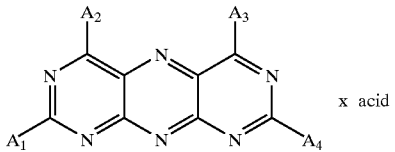

with a base in the presence of a solvent,
with the proviso that when $A_1$, $A_2$, $A_3$ and $A_4$ are $NH_2$, the acid is not phosphoric acid, sulfamic acid or $R_{14}R_{15}NSO_3H$, wherein $R_{14}$ and $R_{15}$ are each independently of the others hydrogen or $C_1$-$C_4$alkyl.

* * * * *